US00PP35110P2

(12) United States Plant Patent
Zaiger et al.

(10) Patent No.: US PP35,110 P2
(45) Date of Patent: Apr. 18, 2023

(54) CHERRY TREE NAMED 'ROYAL BLUSH'

(50) Latin Name: *Prunus avium*
Varietal Denomination: Royal Blush

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 17/300,575

(22) Filed: Aug. 26, 2021

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 5/085
See application file for complete search history.

*Primary Examiner* — Kent L Bell

(57) ABSTRACT

A new and distinct variety of cherry tree (*Prunus avium*). The following features of the tree and its fruit are characterized with the tree budded on 'Mahaleb' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree with a vigorous, upright growth habit.
2. Regular and productive bearer of large size fruit.
3. Fruit with an attractive red blush over yellowish-white skin.
4. Fruit with very good flavor and eating quality with a good balance between acid and sugar.
5. Fruit with good handling and storage quality.

1 Drawing Sheet

Botanical designation: *Prunus avium.*
Variety denomination: 'Royal Blush'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of cherry tree was originated and asexually reproduced by us in our experimental orchard located near Modesto, Stanislaus County, Calif.

PRIOR VARIETIES

Among the existing varieties of cherry trees, which are known to us, and mentioned herein, 'Royal Rainier' Cherry (U.S. Plant Pat. No. 10,790) and our proprietary non-patented cherry selections '23ZM89' and '21ZB487'.

STATEMENT REGARDING FEDERALLY SPONSORED RESEARCH AND DEVELOPMENT

Not applicable.

ORIGIN OF THE VARIETY

The present new variety of cherry tree (*Prunus avium*) was developed by us in our experimental orchard located near Modesto, Calif. as an open pollinated seedling selection from our proprietary cherry seedling '23ZM89'. The seed parent '23ZM89' originated as a second generation seedling from the cross of 'Royal Rainier' Cherry (U.S. Plant Pat. No. 10,790) and our proprietary cherry seedling '21ZB487'. A large number of these open pollinated seedlings were budded and maintained on established 'Mahaleb' Rootstock (non-patented) to accelerate fruit production for evaluation. Under close and careful observation the present seedling exhibited desirable tree and fruit characteristics and was selected in 2012 for additional asexual propagation and commercialization.

ASEXUAL REPRODUCTION OF THE VARIETY

In 2012 asexual reproduction of the new and distinct variety of cherry tree was by budding to 'Mahaleb' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of cherry tree (*Prunus avium*) is of large size, vigorous, upright growth and is a regular and productive bearer of large size, yellowish-white flesh fruit with very good flavor and eating quality. The fruit is further characterized by having an attractive red blush over yellowish-white skin and firm flesh. In comparison to its immediate seed parent '23ZM89' the fruit of the new variety is larger in size and approximately 10 days earlier in maturity. In comparison to the commercial variety 'Royal Rainier' Cherry (U.S. Plant Pat. No. 10,790) the fruit of the new variety is approximately 6 days later in maturity.

DESCRIPTION OF THE PHOTOGRAPH

The accompanying color photographic illustration shows typical specimens of the foliage and fruit of the present new cherry variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 13 year old tree and the colors are as nearly true as is reasonably possible in a color representation of this type.

DESCRIPTION OF THE VARIETY

The following is a detailed botanical description of the new variety of cherry tree, its flowers, foliage and fruit, as based on observations of 13 year old specimens grown near Modesto, Calif., with color in accordance with Munsell Book of Color published in 1958.

Tree:

*Size*.—Large, pruned to 3 to 3.5 meters in height and width for economical harvesting of fruit. Varies with different cultural practices.

*Vigor*.—Vigorous, tree growth of 3 to 3.5 meters the first growing season. Varies with cultural practices, soil type, fertility and climatic conditions.

*Form*.—Upright growth, usually pruned to vase shape.

*Branching habit*.—Upright, crotch angle approximately 35°, increases with heavy crop load.

*Productivity*.—Productive, produces adequate fruit set annually.

*Bearer*.—Regular, adequate fruit set 10 consecutive years. No alternate bearing observed.

*Fertility*.—Self-sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 650 hours at or below 45° F.

Trunk:

*Size*.—Medium. Average circumference 51.2 cm at 26.7 cm above ground on a 13 year old tree.

*Stocky*.—Medium stocky.

*Texture*.—Medium shaggy, roughness increases with age of tree.

*Color*.—Varies from 10YR 4/2 to 10YR 2/2.

Branches:

*Size*.—Medium. Average circumference 21.9 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 15 in a 25.8 square cm area. Average length 4.9 mm. Average width 1.7 mm. Color varies from 10YR 4/8 to 10YR 3/6.

*Color*.—New growth varies from 2.5GY 6/6 to 2.5GY 6/8. Mature growth varies from 10YR 3/2 to 10YR 3/4, varies with age of growth.

Leaves:

*Size*.—Medium to large. Average length 123.1 mm. Average width 53.7 mm.

*Form*.—Ovate.

*Apex*.—Acuminate.

*Base*.—Cuneate.

*Margin*.—Doubly serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 34.5 mm. Average width 1.7 mm. Longitudinally grooved. Surface — glabrous. Color varies from 5GY 7/6 to 5R 3/4.

*Glands*.—Type — reniform. Size — large. Average length 2.8 mm. Average diameter 1.5 mm. Average number 3, varies from 2 to 4. Located primarily on the upper portion of the petiole and base of the leaf blade. Color varies from 10R 3/6 to 10R 2/6.

*Stipules*.—None present at time of measurement.

*Color*.—Upper surface varies from 7.5GY 4/4 to 7.5GY 3/4. Lower surface varies from 5GY 5/4 to 5GY 4/4. Midvein color varies from 5GY 7/4 to 5GY 7/6.

Flower buds:

*Size*.—Large. Average length 17.0 mm. Average diameter 8.4 mm.

*Hardiness*.—Hardy with respect to California winters.

*Density*.—Very dense.

*Form*.—Conical, becoming elongated just before opening.

*Pedicel*.—Average length 13.7 mm. Average width 1.3 mm. Surface — glabrous. Color varies from 2.5GY 5/8 to 5GY 5/8.

*Color*.—N 9.5/(white) with 2.5R 4/8 on some edges.

*Number of buds per spur*.—Average number 9, varies from 5 to 13. Varies with age of spur.

Flowers:

*Blooming period*.—Date of First Bloom Mar. 9, 2020. Date of Petal Fall Mar. 20, 2020, varies slightly with climatic conditions.

*Size*.—Large. Average height 17.7 mm. Average diameter 40.6 mm.

*Petals*.—Number — normally 5, alternately arranged to sepals. Size — large. Average length 19.2 mm. Average width 19.0 mm. Form — orbicular. Arrangement — overlapping. Margin — sinuate. Petal apex — rounded. Petal base — truncate. Color N 9.5/(white). Both upper and lower surfaces glabrous.

*Sepals*.—Number — normally 5, alternately arranged to petals. Size — large. Average length 8.7 mm. Average width 5.5 mm. Shape — triangular to ovate. Apex — triangular to ovate. Margin — entire. Color — upper surface varies from 5GY 5/6 to 5GY 5/8. Lower surface 5GY 5/8 to 7.5R 3/4. Both upper and lower surfaces glabrous.

*Stamens*.—Average number per flower 29. Average filament length 11.3 mm. On average, the stamens are below the height of the petals. Filament color N 9.5/(white). Anther color varies from 5GY 8/8 to 5GY 8/10.

*Pollen*.—Present, self sterile, pollinator required. Color varies from 2.5Y 7/10 to 5Y 7/12.

*Pistil*.—Number — normally 1. Surface — glabrous. Average length 15.9 mm. Position of stigma even in height with the anthers. Color varies from 10Y 7/8 to 2.5GY 7/8.

*Fragrance*.—Wanting.

*Color*.—N 9.5/(white).

*Pedicel*.—Average length 18.5 mm. Average width 1.3 mm. Surface — glabrous. Color varies from 2.5GY 5/8 to 5GY 5/8.

*Number flowers per flower bud*.—Average number 4, varies from 2 to 5.

Fruit

*Maturity when described*.—Firm ripe and ready for consumption.

*Date of first picking*.—May 11, 2020.

*Date of last picking*.—May 21, 2020, varies slightly with climatic conditions.

*Size*.—Large. Average diameter axially 27.7 mm. Average transversely in suture plane 28.1 mm. Average weight 10.0 grams, varies slightly with fertility of the soil, amount of thinning and climatic conditions.

*Form*.—Globose.

*Suture*.—Smooth to very slightly lipped.

*Ventral surface*.—Nearly smooth to slightly lipped.

*Apex*.—Slightly retuse.

*Base*.—Retuse.

*Stem cavity*.—Rounded to slightly elongated in suture plane. Average depth 2.0 mm. Average diameter 3.5 mm.

Stem:

*Size*.—Medium. Average length 37.5 mm. Average diameter 1.9 mm.

*Color*.—Varies from 5GY 5/6 to 7.5GY 5/8.

Flesh:

*Ripens*.—Evenly.

*Texture*.—Firm, meaty.

*Fibers*.—Few, small, tender.

*Firmness*.—Firm, comparable to other commercial cherry varieties.

*Aroma*.—Slight.

*Amydgalin*.—Undetected.

*Eating quality*.—Very good.

*Flavor*.—Very good, with a good balance between acid and sugar.

*Juice*.—Heavy amount, enhances flavor.

*Acidity*.—Not available.

*Brix*.—Average Brix 17.8°, varies slightly with amount of fruit per tree and climatic conditions.

*Color*.—Varies from 5Y 8/4 to 7.5Y 8.5/4.

*Pit cavity*.—Average length 11.9 mm. Average width 10.4 mm. Average depth 4.0 mm. Color varies from 5Y 8/4 to 7.5Y 8.5/4.

Skin:

*Thickness*.—Medium.

*Surface*.—Smooth.

*Bloom*.—Wanting.

*Tendency to crack*.—None during dry weather. Only slight tendency to crack in wet weather.

*Color*.—Ground color varies from 2.5Y 8.5/6 to 2.5Y 8/6. Where fruit exposed to sunlight a blush develops which the color varies from 7.5R 3/12 to 7.5R 4/12.

*Tenacity*.—Tenacious to the flesh.

*Astringency*.—Undetected.

Stone:

*Type*.—Clingstone, medium adherence to flesh.

*Size*.—Medium. Average length 11.4 mm. Average width 9.9 mm. Average thickness 7.9 mm.

*Form*.—Obovoid.

*Base*.—Flat.

*Apex*.—Rounded.

*Surface*.—Very slightly pitted throughout. Small ridges run along suture line from base to apex.

*Sides*.—Varies from equal to unequal with one side extending further from suture plane.

*Ridges*.—Relatively smooth, a small, narrow ridge on each side of suture extending from base to apex.

*Tendency to split*.—None.

*Color*.—Varies from 10YR 6/8 to 10YR 6/10 when dry.

Kernel:

*Size*.—Medium. Average length 7.7 mm. Average width 6.7 mm. Average depth 5.2 mm.

*Form*.—Ovate.

*Viability*.—Viable, complete embryo development.

*Skin color*.—Varies from 5Y 8.5/2 to 10Y 9/2.

Use:

*Dessert*.—Market — local and long distance.

Keeping quality: Good, held firm in cold storage for 3 weeks at 38° to 42° F. without internal breakdown of flesh or appreciable loss of eating quality.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices. The present new variety of cherry tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of cherry tree (*Prunus avium*), substantially as illustrated and described.

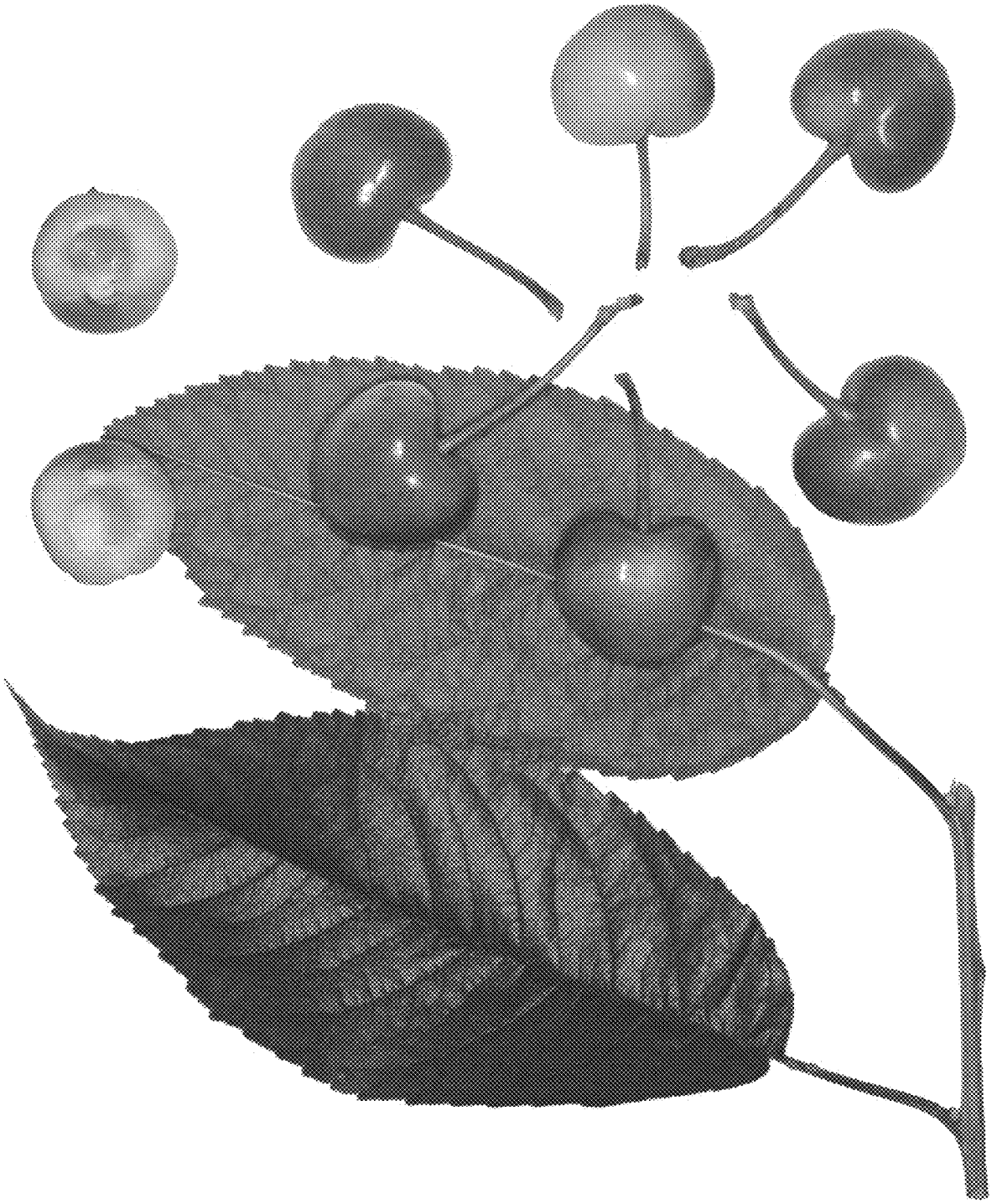

* * * * *